(12) United States Patent
Yamamoto et al.

(10) Patent No.: US 7,388,104 B2
(45) Date of Patent: Jun. 17, 2008

(54) FLUORINATED URETHANE COMPOUNDS AND COMPOSITIONS CONTAINING THE SAME

(75) Inventors: Ikuo Yamamoto, Settsu (JP); Kayo Kusumi, Settsu (JP); Takuya Yoshioka, Settsu (JP); Fumihiko Yamaguchi, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 315 days.

(21) Appl. No.: 10/523,518

(22) PCT Filed: Aug. 5, 2003

(86) PCT No.: PCT/JP03/09903

§ 371 (c)(1),
(2), (4) Date: Feb. 4, 2005

(87) PCT Pub. No.: WO2004/013089

PCT Pub. Date: Feb. 12, 2004

(65) Prior Publication Data

US 2006/0091351 A1 May 4, 2006

(30) Foreign Application Priority Data

Aug. 6, 2002 (JP) ............................. 2002-228795

(51) Int. Cl.
*C07C 271/00* (2006.01)
*D06M 15/19* (2006.01)

(52) U.S. Cl. ........................................ 560/158; 252/8.62

(58) Field of Classification Search ........................ None
See application file for complete search history.

(56) References Cited

U.S. PATENT DOCUMENTS

| | | |
|---|---|---|
| 3,547,894 A | 12/1970 | Smeltz |
| 4,709,074 A | 11/1987 | Bathelt et al. |
| 4,835,300 A | 5/1989 | Fukui et al. |
| 5,171,877 A | 12/1992 | Knaup et al. |
| 5,414,111 A | 5/1995 | Kirchner |
| 5,565,564 A | 10/1996 | Kirchner |
| 5,624,974 A | 4/1997 | Onishi et al. |

FOREIGN PATENT DOCUMENTS

| | | |
|---|---|---|
| DE | 3530967 A1 | 3/1987 |
| EP | 0103752 A2 | 3/1984 |
| EP | 0383365 A2 | 8/1990 |
| EP | 0 435 220 A2 | 7/1991 |
| JP | 63-45665 B2 | 9/1988 |
| JP | 63-60021 B2 | 11/1988 |
| JP | 2-209984 | 8/1990 |
| JP | 2-60702 B2 | 12/1990 |
| JP | 4-321660 A | 11/1992 |
| JP | 5-273899 A | 10/1993 |
| JP | 7-218734 A | 8/1995 |
| JP | 9-281346 A | 10/1997 |
| JP | 10-3011 A | 1/1998 |
| WO | WO 93/17165 A1 | 9/1993 |
| WO | WO 97/25308 A1 | 7/1997 |
| WO | WO 98/51723 A1 | 11/1998 |
| WO | WO 98/51724 A1 | 11/1998 |
| WO | WO 98/51725 A1 | 11/1998 |
| WO | WO 98/51726 A1 | 11/1998 |
| WO | WO 98/51727 A1 | 11/1998 |

*Primary Examiner*—Paul A. Zucker
(74) *Attorney, Agent, or Firm*—Sughrue Mion, PLLC

(57) ABSTRACT

A fluorine-containing urethane compound of the general formula:

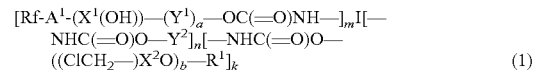

wherein I is a group remaining after an isocyanate group is removed from a polyisocyanate compound, Rf is a perfluoroalkyl group having 2 to 21 carbon atoms, $A^1$ is a direct bond or a divalent organic group having 1 to 21 carbon atoms, $X^1$ and $X^2$ are trivalent linear or branched aliphatic group having 2 to 5 carbon atoms, $Y^1$ is a divalent organic group having 0 to 5 carbon atoms and 0 to 2 nitrogen atoms (provided that at least one carbon atom or nitrogen atom is present) and at least one hydrogen atom, $Y^2$ is a monovalent organic group optionally having a hydroxyl group, and $R^1$ is a hydrogen atom or an alkyl group having 1 to 10 carbon atoms, can impart high water- and oil-repellency.

10 Claims, No Drawings

FLUORINATED URETHANE COMPOUNDS AND COMPOSITIONS CONTAINING THE SAME

TECHNICAL FIELD

The present invention relates to a novel fluorinated urethane compound, and a composition and treatment agent comprising the same. The fluorinated urethane compound of the present invention is suitable for treating (particularly surface-treating) various substrates such as a textile.

BACKGROUND ARTS

Hitherto, various fluorine-containing compounds have been proposed. The fluorine-containing compounds have the advantage that they are excellent in properties such as heat resistance, oxidation resistance and weather resistance. Due to the property that the fluorine-containing compounds have a low free energy, that is, low adhesion, the fluorine-containing compounds have been used, for example, as a water- and oil-repellent agent and a stainproof (or soil release) agent.

The fluorine-containing compounds which can be used as the water- and oil-repellent agent are disclosed in, for example, JP-B-63-60021, JP-B-02-60702, JP-B-02-60702 and JP-B-63-45665. Examples of the fluorine-containing compounds are disclosed also in, for example, U.S. Pat. Nos. 5,414,111, 5,565,564, EP-A-383365, JP-A-07-505190 (WO93/17165), WO97/25308, U.S. Pat. No. 3,547,894, JP-A-2001-525010 (WO98/51727), JP-A-2001-525871 (WO98/51723), JP-A-2001-525872 (WO98/51726), JP-A-2001-525874 (WO98/51724) and JP-A-2002-504938 (WO98/51725).

These fluorine-containing compounds cannot impart sufficient water- and oil-repellency.

DISCLOSURE OF THE INVENTION

The object of the present invention is to provide a novel fluorine-containing compound which can impart high water- and oil-repellency.

The novel fluorine-containing compound of the present invention is a fluorine-containing compound represented by the general formula:

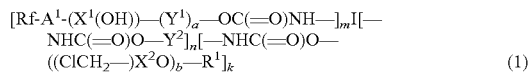

wherein I is a group remaining after an isocyanate group is removed from a polyisocyanate compound,
Rf is a perfluoroalkyl group having 2 to 21 carbon atoms,
$A^1$ is a direct bond or a divalent organic group having 1 to 21 carbon atoms,
$X^1$ and $X^2$ are trivalent linear or branched aliphatic group having 2 to 5 carbon atoms,
$Y^1$ is a divalent organic group having 0 to 5 carbon atoms and 0 to 2 nitrogen atoms (provided that at least one carbon atom or nitrogen atom is present) and at least one hydrogen atom,
$Y^2$ is a monovalent organic group optionally having a hydroxyl group,
$R^1$ is a hydrogen atom or an alkyl group having 1 to 10 carbon atoms,
a is the number of 0 or 1,
b is the number of 1 to 20,
m is the number of 1 to 15,
n and k are the number of 0 to 14, and
the total of m, n and k is the number of 2 to 15.

The present invention provides also a fluorine-containing urethane compound of the general formula:

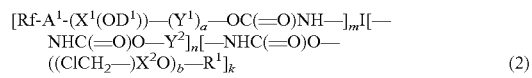

wherein I is a group remaining after an isocyanate group is removed from a polyisocyanate compound,
Rf is a perfluoroalkyl group having 2 to 21 carbon atoms,
$A^1$ is a direct bond or a divalent organic group having 1 to 21 carbon atoms,
$X^1$ and $X^2$ are trivalent linear or branched aliphatic group having 2 to 5 carbon atoms,
$D^1$ is a residue resulting from the reaction between an active hydrogen-reactive compound and active hydrogen of a hydroxyl group,
$Y^1$ is a divalent organic group having 0 to 5 carbon atoms and 0 to 2 nitrogen atoms (provided that at least one carbon atom or nitrogen atom is present) and at least one hydrogen atom,
$Y^2$ is a monovalent organic group optionally having a hydroxyl group,
$R^1$ is a hydrogen atom or an alkyl group having 1 to 10 carbon atoms,
a is the number of 0 or 1,
b is the number of 1 to 20,
m is the number of 1 to 15,
n and k are the number of 0 to 14, and
the total of m, n and k is the number of 2 to 15.

The fluorine-containing urethane compound of the present invention is a compound represent by the formula (1) or (2).

The fluorine-containing urethane compound (1) is explained-hereinafter.

In the formula (1), I is a group remaining after the isocyanate group is removed from the polyisocyanate compound. The polyisocyanate compound is a compound having at least two isocyanate groups. The polyisocyanate compound may be an aliphatic polyisocyanate, an aromatic polyisocyanate, or a derivative of these polyisocyanates.

Examples of the aliphatic polyisocyanate, particularly an aliphatic diisocyanate are hexamethylene diisocyanate, isophorone diisocyanate, xylylene diisocyanate, hydrogenated xylylene diisocyanate, and hydrogenated dicyclohexylmethane diisocyanate. Examples of the aromatic polyisocyanate, particularly an aromatic diisocyanate are tolylene diisocyanate, diphenylmethane diisocyanate (MDI), tolidine diisocyanate and naphthalene diisocyanate.

The polyisocyanate compound is preferably a diisocyanate, polymeric MDI (diphenylmethane diisocyanate), a modified isocyanate (particularly, a trimer of diisocyanate, or an adduct between a polyhydric alcohol and a diisocyanate).

Examples of the modified isocyanate are a urethane-modified diisocyanate, an allophanate-modified diisocyanate, a biuret-modified diisocyanate, an isocyanurate-modified diisocyanate, a carbodiimide-modified diisocyanate, a uretonimine-modified diisocyanate and an acylurea diisocyanate.

Rf is the perfluoroalkyl group having 2 to 21 carbon atoms. The carbon number of Rf may be, for example, from 3 to 12, particularly from 4 to 8.

$A^1$ is a direct bond or a divalent organic group having 1 to 21 carbon atoms.

Examples of the $A^1$ group are of the formula:

—$(CH_2)_p$—

—$CONR^{11}$—$R^{12}$—

—$CH_2C(OH)HCH_2$—

—$CH_2C(OCOR^{13})HCH_2$— or

—O—Ar—$CH_2$— wherein $R^{11}$ is hydrogen or an alkyl group having 1 to 10 carbon atoms,
$R^{12}$ is an alkylene group having 1 to 10 carbon atoms,
$R^{13}$ is hydrogen or a methyl group,
Ar is an arylene group (having, for example, 6 to 20 carbon atoms) optionally having a substituent, and
p is the number of 1 to 10. $A^1$ may be particularly an alkylene group having 1 to 5 carbon atoms.

$X^1$ and $X^2$ are a trivalent linear or branched aliphatic group having 2 to 5 carbon atoms. Examples of —$(X^1(OH))$— and —$(X^2(OH))$— are —$CH_2CH(OH)$—, —$CH(OH)CH_2$—, —$CH_2CH_2CH(OH)$—, —$CH_2CH(OH)CH_2$—, —$CH(OH)CH_2$—$CH_2$— and —$CH(OH)$—

$Y^1$ is a divalent organic group having 0 to 5 carbon atoms and 0 to 2 nitrogen atoms (provided that at least one carbon atom or nitrogen atom is present) and at least one hydrogen atom. Generally, $Y^1$ is a divalent organic group remaining after an active atom (for example, a hydrogen atom and a halogen atom (particularly, a chlorine atom and a bromine atom)) is removed from a spacer compound. $Y^1$ is represented by, for example, the formula:

—$(NH)_p$—$(CH_2)_q$—$(NH)_r$— wherein p and r are 0 or 1, and q is the number of 0 to 5, for example, 1 to 5. Examples of $Y^1$ are —$CH_2$—, —$(CH_2)_2$—, —$(CH_2)_3$—, —NH—$(CH_2)_2$—NH— and —NH—$(CH_2)_3$—NH—.

$Y^2$ is a monovalent organic group optionally having a hydroxyl group. $Y^2$ is represented by, for example, the formula:

H—$(O)_s$—$(CH_2)_t$— wherein s is 0 or 1, and t is the number of 1 to 5. Examples of $Y^2$ are $CH_3$—, $H(CH_2)_2$—, $H(CH_2)_3$—, HO—$CH_2$—, HO—$(CH_2)_2$— and HO—$(CH_2)_3$—.

$R^1$ is a hydrogen atom or an alkyl group having 1 to 10 carbon atoms. Examples of $R^1$ which is the alkyl group are methyl, ethyl and propyl.

b is the number of 1 to 20. b may be, for example, from 2 to 15, particularly from 2 to 10.

m is the number of 1 to 15. m may be, for example, from 2 to 10, particularly from 2 to 3.

n and k are the number of 0 to 14. n and k may be, for example, from 0 to 10, particularly from 1 to 8.

The total of m, n and k is the number of 2 to 15. The total of m, n and k may be, for example, from 2 to 10, particularly from 2 to 3.

Specific examples of the fluorine-containing urethane compound (1) of the present invention are as follows:

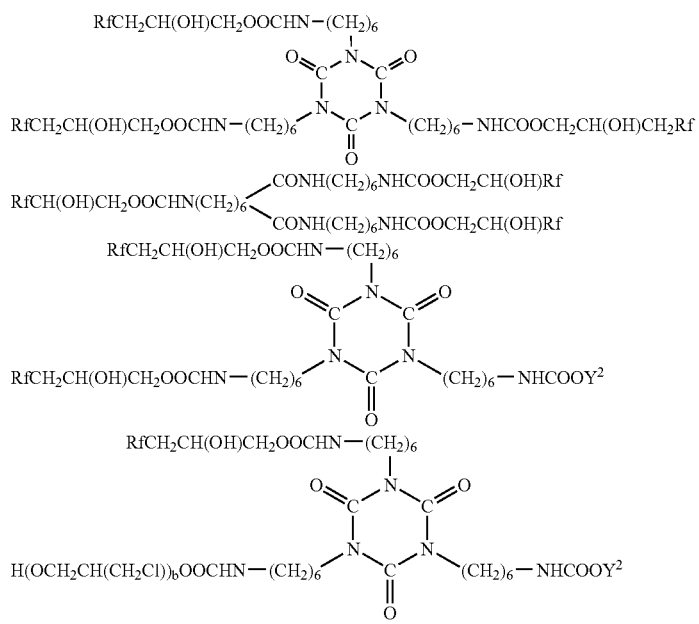

wherein Rf, $Y^2$ and b are the same as defined above.

The fluorine-containing urethane compound (1) of the present invention can be obtained, for example, by reacting a polyisocyanate compound with a diol of the formula:

$$Rf-A^1-(X^1(OH))—(Y^1)_a—OH \qquad (i)$$

and, optionally present, an alcohol of the formula:

$$HO—Y^2 \qquad (ii)$$

and a chlorine-containing ether alcohol of the formula:

 (iii).

wherein Rf, $A^1$, $X^1$, $X^2$, $Y^1$, $Y^2$, $R^1$, a and b are the same defined above.

In this reaction, the total amount of the diol (i), the alcohol (ii) and the chlorine-containing ether alcohol (iii) is preferably from 0.5 mol to 2.0 mol, particularly from 0.8 mol to 1.5 mol, based on 1 mol of isocyanate group in the polyisocyanate compound. The alcohol (ii) and the chlorine-containing ether alcohol (iii) are a component which may be used or may not be used. This reaction is preferably conducted in the presence of a solvent at 0° C. to 150° C. for 0.1 hours to 10 hours. The solvent is an organic solvent which is inert to the isocyanate. Examples of the solvent are a hydrocarbon, a ketone and a halogenated hydrocarbon (for example, a chlorine-containing hydrocarbon). The amount of the solvent may be from 20 to 500 parts by weight, for example, from 100 to 300 parts by weight, based on 100 parts by weight of the reactants.

A catalyst is preferably used in the reaction. Examples of the catalyst are an amine (for example, a monoamine, a diamine, a triamine, an alcohol amine, and an ether amine), and an organic metal (for example, a metal salt of an organic acid such as di-n-butyl tin dilaurate). The amount of the catalyst may be from 0.001 to 0.5 parts by weight, for example, from 0.01 to 0.3 parts by weight, based on 100 parts by weight of the reactants.

The diol (i) can be obtained, for example, by hydrolyzing a fluorine-containing cyclic ether compound of the formula:

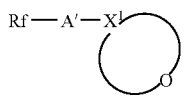

wherein Rf, $A^1$ and $X^1$ are the same as defined above, and then optionally reacting the resultant with a spacer compound.

The fluorine-containing cyclic ether compound is, for example, an oxirane compound or an oxetane compound.

The spacer compound is a compound having an active atom (for example, a hydrogen atom, a chlorine atom and a bromine atom). Examples of the spacer compound include a diamine and a halogenated hydrocarbon. Specific examples of the spacer compound are an alkyl diamine (for example, ethylene diamine and propylene diamine) and a linear hydrocarbon having halogen atoms at both ends.

The alcohol (ii) may be a monohydric alcohol or a polyhydric (for example, di- to penta-hydric) alcohol. The examples of the alcohol (ii) are an aliphatic alcohol, an aromatic alcohol. Specific examples of the alcohol (ii) are ethanol, propanol, ditripropylene glycol, trimethylol propane, pentaerythritol, phenol and hyrdoxytoluene.

The chlorine-containing ether alcohol (iii) can be obtained, for example, by polymerizing a chlorine-containing ether compound of the formula:

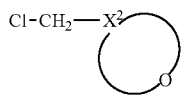

wherein $X^2$ is the same as defined above. An example of the chlorine-containing ether compound is epichlorohydrin.

Hereinafter, the fluorine-containing urethane compound (2) is explained.

In the formula (2), $D^1$ is a residue obtained by reacting an active hydrogen-reactive compound with active hydrogen of a hydroxyl group. Examples of the active hydrogen-reactive compound are an isocyanate compound [particularly, a monoisocyanate of the formula: R—NCO wherein R is an organic group (for example, a hydrocarbon group)], an epoxy compound, and a carboxylic acid compound.

Specific examples of the fluorine-containing urethane compound (2) of the present invention are as follows:

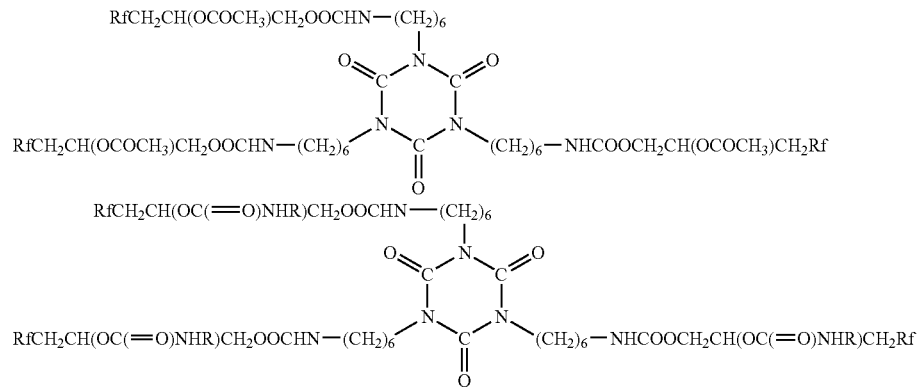

wherein Rf is a perfluoroalkyl group having 2 to 21 carbon atoms, and R is group remaining after one isocyanate group is removed from an isocyanate compound.

The fluorine-containing urethane compound (2) of the present invention can be prepared by the same procedure as in the fluorine-containing urethane compound (1) except that a diol of the formula:

wherein Rf, $A^1$, $X^1$, $D^1$, $Y^1$, $Y^2$ and a are the same as defined above, is used instead of the diol (i).

The diol (i') can be prepared by modifying (for example, acetylating or urethanizing) a secondary hydroxyl group of the diol (i). Examples of a modifying agent are a carboxylic acid, and an isocyanate (R—NCO) [wherein R is an organic group (for example, a hydrocarbon group)].

The fluorine-containing urethane of the present invention may be contained in a composition. The composition may be in the form of a solution or an emulsion. The solution-type composition comprises the fluorine-containing urethane compound and a solvent. Examples of the solvent (particularly, an organic solvent) in the solution-type composition are a hydrocarbon, a ketone, and a halogenated hydrocarbon (for example, a chloride-containing hydrocarbon). The emulsion-type composition comprises the fluorine-containing urethane compound, an emulsifier and water. The emulsion-type composition may further contain an organic solvent, particularly an organic solvent which dissolves the fluorine-containing urethane compound. The emulsifier may be any of nonionic and ionic (for example, cationic, anionic and amphoteric).

The amount of the fluorine-containing urethane compound may be from 0.1 to 70% by weight, for example, from 5 to 30% by weight, based on the composition. In the emulsion-type composition, relative to 100 parts by weight of the fluorine-containing urethane compound, the amount of the emulsifier may be from 0.1 to 30 parts by weight, for example, from 2 to 10 parts by weight, the amount of water may be from 30 to 99.9 parts by weight, for example, from 70 to 95 parts by weight, the amount of the organic solvent may be from 10 to 200 parts by weight, for example, from 50 to 100 parts by weight.

The fluorine-containing urethane compound of the present invention can be used as a surface treatment agent which treats surfaces of various articles so that the surfaces of articles are modified, to have, for example, water- and oil-repellency.

The fluorine-containing urethane compound of the present invention has excellent water- and oil-repellency, is rich in molecular stability and has high durability. Therefore, when a substrate is treated with the fluorine-containing urethane compound, the substrate can maintain excellent properties for a long term.

When the treatment is conducted, an arbitrary method can be adopted depending on the form of the surface treatment agent. For example, when an aqueous emulsion-type surface treatment agent or a solvent solution-type surface treatment agent is used, the treatment liquid is adhered to at least surface of the substrate by a procedure such as a dip coating procedure and then dried. In the case of the emulsion-type surface treatment agent, after the drying, the curing is desirably conducted for the purpose of the continuation of treatment agent fine particles and the penetration into and the melt-adhesion to the substrate. Thus, high water- and oil-repellency effect can be expected. The solution-type treatment agent has the advantage that sufficiently high water- and oil-repellency can be expected without the curing and washing, since a coating film is formed on the substrate by the drying. If necessary, the curing may be conducted. The dry temperature is arbitrarily selected, but the dry temperature may be a normal temperature and the drying at 50 to 120° C. by hot air is effective in the case of the emulsion-type treatment agent. In the case of the solution-type treatment agent, it is suitable to dry at about 50 to 150° C.

The substrate to be treated with the surface treatment agent of the present invention includes various materials. Examples of the substrate include textile, glass, paper, wood, leather, fur, asbestos, brick, cement, metal and oxide, ceramics, plastic, coated surface and plaster.

In the present invention, the substrate to be treated is preferably a textile, for example, a carpet. Examples of the textile are various. Examples of the textile include animal- or vegetable-origin natural fibers such as cotton, hemp, wool and silk; synthetic fibers such as polyamide, polyester, polyvinyl alcohol, polyacrylonitrile, polyvinyl chloride and polypropylene; semisynthetic fibers such as rayon and acetate; inorganic fibers such as glass fiber, carbon fiber and asbestos fiber; and a mixture of these fibers.

The textile may be in any form such as a fiber, a yarn and a fabric. When the carpet is treated according to the method of the present invention, the carpet may be formed after treating fibers or yarns with the surface treatment agent, or the formed carpet may be treated with the surface treatment agent. The surface treatment agent can contain the fluorine-containing urethane compound which is in the diluted state of 0.02 to 30% by weight, preferably 0.02 to 10% by weight.

Hereinafter, the present invention is illustrated hereinafter.

SYNTHESIS EXAMPLE 1

Synthesis of a Fluorine-containing Diol:

A fluorine-containing epoxy (750 g (1.57 mol)) of the formula:

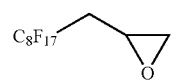

acetic acid (179 ml (3.14 mol)) and triethylamine (12 ml (0.09 mol)) were charged into a 2 L four-necked flask and reacted at an internal temperature of 95 to 100° C. for 10 hours with stirring to give an acetylated product. A GC analysis confirmed that the conversion was 99% and the purity was 94.5%.

After cooling to room temperature, a solution of potassium hydroxide (135 g (1.92 mol)) dissolved in methanol (450 mL) was added and the mixture was stirred at room temperature for 2 hours. A GC analysis confirmed that the conversion was 94% and the purity was 89%.

Water (2.3 L) was added to the reaction liquid, and a precipitated solid was filtered, and then the same procedure using the same amount of water was repeated. After the precipitated solid was dried, the solid was dissolved in ethanol (300 mL) and active carbon (0.75 g) was added to the solution. The active carbon was filtered off, a filtrate was poured into dichloromethane (2.3 L) and a precipitated crystal was filtered to give an objected product (a fluorine-containing diol):

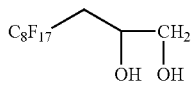

(Yield: 609 g and 89%).

A GC analysis confirmed that the purity was 99%. The structure was confirmed by $^1$H NMR and $^{19}$F NMR.

PREPARATION EXAMPLE 1

Preparation of a Fluorine-containing Urethane (1)

The fluorine-containing diol (20.1 g (40.6 mmol)) obtained in Synthesis Example 1, di-n-butyl tin dilaurate (0.80 g) and butyl isobutyl ketone (35 g) were charged into a 200 mL four-necked flask equipped with a stirrer, a thermometer, a nitrogen-inlet tube, a condenser and a dropping funnel, and stirred. Then, a solution of an isocyanurate-modified hexamethylene diisocyanate:

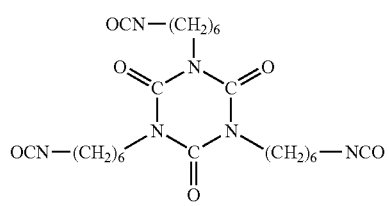

(Sumidur N-3300 manufactured by Sumika Bayer Urethane Co. Ltd., Isocyanate content: 21.8%) (7.79 g (40.6 mmol)) dissolved in methyl isobutyl ketone (10 g) was dropwise added from the dropping funnel for 30 minutes. After the completion of the dropwise addition, the mixture was reacted for 1 hour and an infrared spectrometer confirmed that an isocyanate group was absent. The reaction was controlled at 75° C., and conducted under a nitrogen gas stream. After the completion of the reaction, the organic solvent was evaporated off to give a white crystalline product:

(Yield: 25.3 g and 91%). The structure of the resultant product was confirmed by $^1$H NMR and $^{19}$F NMR.

PREPARATION EXAMPLE 2

Preparation of a Fluorine-containing Urethane (2):

The fluorine-containing diol (20.1 g (40.6 mmol)) obtained in Synthesis Example 1, di-n-butyl tin dilaurate (0.80 g) and butyl isobutyl ketone (35 g) were charged into a 200 mL four-necked flask equipped with a stirrer, a thermometer, a nitrogen-inlet tube, a condenser and a dropping funnel, and stirred. Then, a solution of a biuret-modified hexamethylene diisocyanate: $OCN(CH_2)_6N[CONH(CH_2)_6NCO]_2$ (Sumidur N-3200 manufactured by Sumika Bayer Urethane Co. Ltd., Isocyanate content: 23%) (7.43 g (40.6 mmol)) dissolved in methyl isobutyl ketone (10 g) was dropwise added from the dropping funnel for 30 minutes. After the completion of the dropwise addition, the mixture was reacted for 1 hour and an infrared spectrometer confirmed that an isocyanate group was absent. The reaction was controlled at 75° C., and conducted under a nitrogen gas stream. After the completion of the reaction, the organic solvent was evaporated off to give a white crystalline product:

(Yield: 24.6 g and 89%). The structure of the resultant product was confirmed by $^1$H NMR and $^{19}$F NMR.

COMPARATIVE PREPARATION EXAMPLE 1

Preparation of a Fluorine-containing Urethane (3):

The same isocyanurate-modified hexamethylene diisocyanate (Sumidur N-3300 manufactured by Sumika Bayer Urethane Co. Ltd.) (20.75 g (107.7 mmol)) as used in Preparation Example 1, di-n-butyl tin dilaurate (0.15 g) and butyl isobutyl ketone (57 g) were charged into a 200 mL four-necked flask equipped with a stirrer, a thermometer, a nitrogen-inlet tube, a condenser and a dropping funnel, and stirred. Then, a solution of a fluorine-containing alcohol ($C_8F_{17}CH_2CH_2OH$) (50 g (107.8 mmol)) dissolved in methyl isobutyl ketone (50 g) was dropwise added from the dropping funnel for 30 minutes. After the completion of the dropwise addition, the mixture was reacted for 4 hours and an infrared spectrometer confirmed that an isocyanate group was absent. The reaction was controlled at 75° C., and conducted under a nitrogen gas stream. After the completion of the reaction, the organic

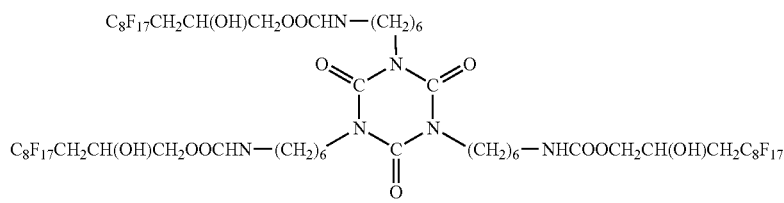

solvent was evaporated off to give a white crystalline product (Yield: 68 g and 97%). $^1$H NMR and $^{19}$F NMR confirmed that the structure of the resultant product was:

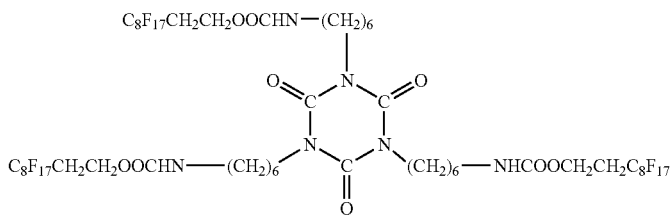

COMPARATIVE PREPARATION EXAMPLE 2

Preparation of a Fluorine-containing Urethane (4):

The same biuret-modified hexamethylene diisocyanate (Sumidur N-3200 manufactured by Sumika Bayer Urethane Co. Ltd.) (19.67 g (107.7 mmol)) as used in Preparation Example 2, di-n-butyl tin dilaurate (0.15 g) and butyl isobutyl ketone (54 g) were charged into a 200 mL four-necked flask equipped with a stirrer, a thermometer, a nitrogen-inlet tube, a condenser and a dropping funnel, and stirred. Then, a solution of a fluorine-containing alcohol ($C_8F_{17}CH_2CH_2OH$) (50 g (107.8 mmol)) dissolved in methyl isobutyl ketone (50 g) was dropwise added from the dropping funnel for 30 minutes. After the completion of the dropwise addition, the mixture was reacted for 3 hours and an infrared spectrometer confirmed that an isocyanate group was absent. The reaction was controlled at 75° C., and conducted under a nitrogen gas stream. After the completion of the reaction, the organic solvent was evaporated off to give a white crystalline product:

(Yield: 68 g and 98%). The structure of the resultant product was confirmed by $^1$H NMR and $^{19}$F NMR.

Water Repellency Test

A carpet treated for giving repellency is stored in a thermohygrostat having a temperature of 21° C. and a humidity of 65% for at least 4 hours. A test liquid (isopropyl alcohol (IPA), water and a mixture thereof having the composition shown in Table 1) which has been also stored at 21° C. is used. The test is conducted in a temperature- and humidity-controlled room at a temperature of 21° C. and a humidity of 65%. Five droplets of the test liquid in an amount of 50 µL are softly dropped by a micropipette on the carpet. If 4 or 5 droplets remain on the carpet after standing for 10 seconds, it is evaluated that the test liquid passes the test. The maximum content of IPA (% by volume) in the test liquid which passes the test is taken as the result of the water repellency. The water repellency is evaluated as twelve levels of Fail, 0, 1, 2, 3, 4, 5, 6, 7, 8, 9 and 10 which are from poor water repellency to excellent water repellency.

TABLE 1

| | Water repellency test liquid | |
| | (volume ratio %) | |
| Point | Isopropyl alcohol | Water |
| --- | --- | --- |
| 10 | 100 | 0 |
| 9 | 90 | 10 |
| 8 | 80 | 20 |
| 7 | 70 | 30 |
| 6 | 60 | 40 |
| 5 | 50 | 50 |
| 4 | 40 | 60 |
| 3 | 30 | 70 |
| 2 | 20 | 80 |
| 1 | 10 | 90 |
| 0 | 0 | 100 |
| Fail | Inferior to isopropyl alcohol 0/water 100 | |

Oil Repellency Test

A carpet treated for giving repellency is stored in a thermohygrostat having a temperature of 21+ C. and a humidity of 65% for at least 4 hours. A test liquid (having the composition shown in Table 2) which has been also stored at 21° C. is used. The test is conducted in a temperature- and humidity-controlled room at a temperature of 21° C. and a humidity of 65%. Five droplets (50 µL) of the test liquid shown in Table 2 are softly dropped on a carpet and the penetration state after 30 seconds is observed. If four or five droplets remain on the carpet, the test liquid passes the test. A maximum point of passing test liquids is taken as the oil repellency. The oil repellency is evaluated as nine levels of Fail, 1, 2, 3, 4, 5, 6, 7, 8 which are from poor oil repellency to excellent oil repellency.

TABLE 2

| | Oil repellency test liquid | |
| Point | Test liquid | Surface tension (dyne/cm, 25° C.) |
| --- | --- | --- |
| 8 | n-heptane | 20.0 |
| 7 | n-octane | 21.8 |
| 6 | n-decane | 23.5 |
| 5 | n-dodecane | 25.0 |
| 4 | n-tetradecane | 26.7 |
| 3 | n-hexadecane | 27.3 |
| 2 | Mixture liquid of n-Hexadecane 35/nujol 65 | 29.6 |

TABLE 2-continued

Oil repellency test liquid

| Point | Test liquid | Surface tension (dyne/cm, 25° C.) |
|---|---|---|
| 1 | Nujol | 31.2 |
| Fail | Inferior to 1 | — |

Stainproof Property Test

The stainproof property test is conducted in accordance with AATCC Test Method 123-1989.

The stainproof property is evaluated by comparing a carpet sample subjected to the stainproof property test with a carpet sample subjected to no stainproof property test by a gray scale for discoloration. The stainproof property is evaluated as nine levels of 1, 1-2, 2, 2-3, 3, 3-4, 4, 4-5 and 5 which are from remarkable discoloration to no discoloration.

EXAMPLE 1

The fluorine-containing urethane compound (1) synthesized in Preparation Example 1 (5 g) and methyl isobutyl ketone (MIBK) (5 g) are mixed and heated at 75° C. to 80° C. for 10 minutes. Pure water (14.4 g), polyoxyethylene alkyl ether (nonionic emulsifier) (0.5 g) and sodium a-olefin sulfonate (anionic emulsifier) (0.1 g) were mixed in another vessel and heated at 75° C. to 80° C. for 10 minutes. These two liquids were mixed and emulsified by an ultrasonic emulsifier.

Water (97.5 g) was added to the resultant emulsion (2.5 g) to give a mixture having the total weight of 100 g which was taken as a treatment liquid. A carpet (20 cm×20 cm, Nylon 6, cut pile (density: 32 oz/yd$^2$)) was spray-treated with this treatment liquid at WPU (wet pick up, WPU is 20% when 20 g of a liquid is positioned onto 100 g of a carpet) amount of 20%. Then heat cure was conducted at 120° C. for 10 minutes.

Then a water repellency test, an oil repellency test and a stainproof property test were performed. The results are shown in Table 3.

EXAMPLE 2

The fluorine-containing urethane compound (2) synthesized in Preparation Example 2 was emulsified as in Example 1. Water (97.5 g) was added to the resultant emulsion (2.5 g) to give a mixture having the total weight of 100 g which was taken as a treatment liquid. A carpet was treated with the resultant repellent agent as in Example 1.

Then a water repellency test, an oil repellency test and a stainproof property test were performed. The results are shown in Table 3.

COMPARATIVE EXAMPLE 1

The fluorine-containing urethane compound (3) synthesized in Comparative Preparation Example 1 was emulsified as in Example 1. Water (97.5 g) was added to the resultant emulsion (2.5 g) to give a mixture having the total weight of 100 g which was taken as a treatment liquid. A carpet was treated with the resultant repellent agent as in Example 1.

Then a water repellency test, an oil repellency test and a stainproof property test were performed. The results are shown in Table 3.

COMPARATIVE EXAMPLE 2

The fluorine-containing urethane compound (4) synthesized in Comparative Preparation Example 2 was emulsified as in Example 1. Water (97.5 g) was added to the resultant emulsion (2.5 g) to give a mixture having the total weight of 100 g which was taken as a treatment liquid. A carpet was treated with the resultant repellent agent as in Example 1.

Then a water repellency test, an oil repellency test and a stainproof property test were performed. The results are shown in Table 3.

TABLE 3

| | | Water repellency | Oil repellency | Stainproof property |
|---|---|---|---|---|
| Example 1 | Preparation Example 1 | 3 | 1 | 5 |
| Example 2 | Preparation Example 2 | 3 | 1 | 5 |
| Comparative Example 1 | Preparation Example 3 | 3 | 1 | 4 |
| Comparative Example 2 | Preparation Example 4 | 3 | 1 | 4 |

EFFECT OF THE INVENTION

The fluorine-containing urethane compound of the present imparts various excellent properties to a substrate as a component of a surface treatment agent.

The invention claimed is:

1. A fluorine-containing urethane compound of the general formula:

$$[Rf\text{-}A^1\text{-}(X^1(OH))\text{---}(Y^1)_a\text{---}OC(\text{=}O)NH\text{---}]_m I[\text{---}NHC(\text{=}O)O\text{---}Y^2]_n[\text{---}NHC(\text{=}O)O\text{---}((ClCH_2\text{---})X^2O)_b\text{---}R^1]_k \quad (1)$$

wherein I is a group remaining after an isocyanate group is removed from a polyisocyanate compound selected from the group consisting of an aliphatic polyisocyanate and an aromatic polyisocyanate, Rf is a perfluoroalkyl group having 2 to 21 carbon atoms, $A^1$ is a direct bond or a divalent organic group having 1 to 21 carbon atoms, of the formula:

—$(CH_2)_p$—

—$CONR$—$R^{11}$—$R^{12}$—

—$CH_2C(OH)HCH_2$—

—$CH_2C(OCOR^{13})HCH_2$— or

—O—Ar—$CH_2$— wherein $R^{11}$ is hydrogen or an alkyl group having 1 to 10 carbon atoms, $R^{12}$ is an alkylene group having 1 to 10 carbon atoms, $R^{13}$ is hydrogen or a methyl group, Ar is an arylene group having 6 to 20 carbon atoms optionally having a substituent, and p is the number of 1 to 10, $X^1$ and $X^2$ are trivalent linear or branched aliphatic group having 2 to 5 carbon atoms, $Y^1$ is a divalent organic group having 0 to 5 carbon atoms and 0 to 2 nitrogen atoms (provided that at least one carbon atom or nitrogen atom is present) and at least one hydrogen atom, $Y^2$ is a monovalent organic group optionally having a hydroxyl group, $R^1$ is a hydrogen atom or an alkyl group having 1 to 10 carbon atoms, a is the number of 0 or 1, b is the number of 1 to 20, m is the number of 1 to 15, n and k are the number of 0 to 14, and the total of m, n and k is the number of 2 to 15.

2. The fluorine-containing urethane compound according to claim 1, wherein the polyisocyanate compound constituting the I group is an aliphatic polyisocyanate, an aromatic polyisocyanate, or a derivative of these polyisocyanates.

3. The fluorine-containing urethane compound according to claim 1, wherein the polyisocyanate compound constituting the I group is a diisocyanate, a polymeric diphenylmethane diisocyanate, or a modified isocyanate.

4. A fluorine-containing urethane compound of the general formula:

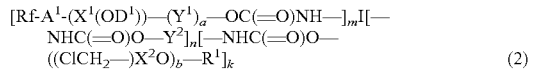  (2)

wherein I is a group remaining after an isocyanate group is removed from a polyisocyanate compound selected from the group consisting of an aliphatic polyisocyanate and an aromatic polyisocyanate, Rf is a perfluoroalkyl group having 2 to 21 carbon atoms, $A^1$ is a direct bond or a divalent organic group having 1 to 21 carbon atoms, of the formula:

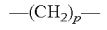

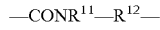

, or

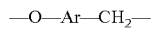

wherein $R^{11}$ is hydrogen or an alkyl group having 1 to 10 carbon atoms, $R^{12}$ is an alkylene group having 1 to 10 carbon atoms, $R^{13}$ is hydrogen or a methyl group, Ar is an arylene group having 6 to 20 carbon atoms optionally having a substituent, and p is the number of 1 to 10

$X^1$ and $X^2$ are trivalent linear or branched aliphatic group having 2 to 5 carbon atoms, $D^1$ is a residue resulting from the reaction between an active hydrogen-reactive compound and active hydrogen of a hydroxyl group, $Y^1$ is a divalent organic group having 0 to 5 carbon atoms and 0 to 2 nitrogen atoms (provided that at least one carbon atom or nitrogen atom is present) and at least one hydrogen atom, $Y^2$ is a monovalent organic group optionally having a hydroxyl group, $R^1$ is a hydrogen atom or an alkyl group having 1 to 10 carbon atoms, a is the number of 0 or 1, b is the number of 1 to 20, m is the number of 1 to 15, n and k are the number of 0 to 14 provided that at least one of n and k is 1 to 8, and the total of m, n and k is the number of 2 to 15.

5. A composition comprising the fluorine-containing urethane compound according to claim 1, an emulsifying agent and water.

6. A treatment agent for treating a textile comprising the composition according to claim 5.

7. A method of treating a textile which comprises treating the textile with the treatment agent according to claim 6.

8. A composition comprising the fluorine-containing urethane compound according to claim 4, an emulsifying agent and water.

9. A treatment agent for treating a textile comprising the composition according to claim 8.

10. A method of treating a textile which comprises treating the textile with the treatment agent according to claim 9.

* * * * *